(12) United States Patent
Deruyttere et al.

(10) Patent No.: US 9,272,989 B2
(45) Date of Patent: Mar. 1, 2016

(54) RADIATION CURABLE AMINO(METH)ACRYLATES

(75) Inventors: Xavier Deruyttere, Sint-Pieters-Leeuw (BE); Thierry Randoux, Braine-L'Alleud (BE); Jean-Yves Salviato, Les Bons Villers (BE); Luc De Waele, Denderwindeke (BE)

(73) Assignee: ALLNEX BELGIUM S.A., Brussels (BE)

( * ) Notice: Subject to any disclaimer, the term of this patent is extended or adjusted under 35 U.S.C. 154(b) by 490 days.

(21) Appl. No.: 13/576,474

(22) PCT Filed: Apr. 11, 2011

(86) PCT No.: PCT/EP2011/055604
§ 371 (c)(1),
(2), (4) Date: Aug. 1, 2012

(87) PCT Pub. No.: WO2011/131501
PCT Pub. Date: Oct. 27, 2011

(65) Prior Publication Data
US 2012/0308734 A1 Dec. 6, 2012

(30) Foreign Application Priority Data
Apr. 19, 2010 (EP) .................................... 10160332

(51) Int. Cl.
| | | |
|---|---|---|
| C07C 271/28 | (2006.01) | |
| C07C 229/12 | (2006.01) | |
| C08F 220/34 | (2006.01) | |
| C08G 18/67 | (2006.01) | |
| C09D 4/06 | (2006.01) | |
| C09D 175/16 | (2006.01) | |
| A01N 43/90 | (2006.01) | |

(52) U.S. Cl.
CPC ............. *C07C 271/28* (2013.01); *C07C 229/12* (2013.01); *C08F 220/34* (2013.01); *C08G 18/672* (2013.01); *C09D 4/06* (2013.01); *C09D 175/16* (2013.01); *A01N 43/90* (2013.01)

(58) Field of Classification Search
CPC .................................. A01N 43/90; C09D 4/00
See application file for complete search history.

(56) References Cited

U.S. PATENT DOCUMENTS

| | | | | |
|---|---|---|---|---|
| 5,648,173 | A | * | 7/1997 | Blizzard ....................... 428/446 |
| 2009/0098304 | A1 | * | 4/2009 | Stone et al. ................... 427/516 |
| 2011/0172175 | A1 | * | 7/2011 | Chow et al. ..................... 514/31 |

FOREIGN PATENT DOCUMENTS

| | | | |
|---|---|---|---|
| JP | H08-259660 | | 10/1996 |
| JP | 2002-60442 | | 2/2002 |
| JP | 2004-511537 | | 4/2004 |
| JP | 2004-196864 | | 7/2004 |
| JP | 2008-545859 | | 12/2008 |
| JP | 2009-541553 | | 11/2009 |
| WO | 02/23851 | | 4/2002 |
| WO | 02/32851 | | 4/2002 |
| WO | WO 2006060272 | * | 6/2006 |
| WO | 2006/131259 | | 12/2006 |
| WO | 2008/000696 | | 1/2008 |
| WO | 2008/076665 | | 6/2008 |

OTHER PUBLICATIONS

S. Velankar et al High performance UV-curable urethane acrylates via deblocking chemistry, J. Appl. Polym. Sci., 62/9 (1996), pp. 1361-1376, Sep. 1996.*
"Industrial Coatings Radcure Energy Curable Resins", 2008, Cytec Surface Specialties, S.A., Drogenbos, XP002587196, pp. 1-32.

* cited by examiner

*Primary Examiner* — Gregory Listvoyb
(74) *Attorney, Agent, or Firm* — Wenderoth, Lind & Ponack, L.L.P.

(57) ABSTRACT

The invention relates to amino(meth)acrylates obtained from the reaction of amines with a mixture of urethane(meth)acrylates and (meth)acrylated diluent sand their use for making coatings, adhesives, varnishes and inks. The amino(meth)acrylates of the invention are particularly suited for use in sealer compositions for parquet and laminate floors.

13 Claims, No Drawings

RADIATION CURABLE AMINO(METH)ACRYLATES

The present invention relates to amino(meth)acrylates obtained from the addition reaction of (meth)acrylates and amines and to their use in radiation curable compositions suitable for industrial coatings.

As wood has a natural beauty and gives a warm ambiance in a living room, wood floorings have always had a lot of success. Wood or laminate flooring is a demanding application, and requires a very good wear resistance. The wear resistance will depend both on core material and on coating performance.

Radiation curable compositions have been used for many years and gained an excellent reputation in parquet and laminate finishing because of their excellent scratch and wear resistance. UV/EB curing also allows for a very cost-effective and lean production process. In fact, panels can be roller-coated with solvent free 100% solids systems, followed by an immediate on-line UV/EB curing step.

A good abrasion resistance, and in particular a good resistance against the wearing effect of fine hard particles like sand, is highly desirable for parquet and laminate floorings. Special urethane(meth)acrylates have been developed for this kind of abrasion resistance and are commercially available.

There is however a continued demand in the market for urethane(meth)acrylates that permit to obtain coatings with improved curing reactivity in combination with e.g. an excellent adhesion, scratch resistance and abrasion resistance. There is a further demand for urethane(meth)acrylates that have a reactivity fitting with typical wood coating line speeds of about 25 to 30 m/min.

The amination of (meth)acrylate compounds is known. For instance, WO 02/32851 describes the use of DMA (dimethylamine) for the amination of $\alpha,\beta$-unsaturated esters that are obtained by reacting (meth)acrylic acid with an alcohol or polyol. The amine/$\alpha,\beta$-unsaturated ester adduct can be radiation cured in blend with a polymer precursor like a urethane (meth)acrylate. However, as the amine/$\alpha,\beta$-unsaturated ester adduct is free of residual amine, no amination of the urethane (meth)acrylate occurs in WO 02/32851.

Against this background we now provide amino(meth) acrylates obtained from the reaction of at least one amine (A) with a mixture (M) comprising from 15 to 99% by weight of at least one urethane(meth)acrylate (B) and from 1 to 85% by weight of at least one (meth)acrylated diluent (C).

In the present invention, the term "(meth)acryl" is to be understood as to encompass both acryl and methacryl compounds or derivatives as well as mixtures thereof. By "(meth) acrylated" compounds is meant more in particular compounds comprising at least one acrylate (CH2=CHCOO—) group and/or at least one methacrylate (CH2=CCH3COO—) group. When both acrylate groups and methacrylate groups are present, they can be present on the same or on different compounds.

The amine (A) used to prepare the amino(meth)acrylates of the present can be selected from primary and/or secondary amines. The amine (A) used to prepare the amino(meth) acrylates of the present invention is generally selected from primary amines (A1) comprising at least one primary amino group —$NH_2$ and/or from secondary amines (A2) comprising at least two secondary amino groups —NH. The use of such secondary amines (A2) has the advantage that they allow chain extension. By chain extension is meant a reaction by which at least two (meth)acrylate compounds (B), or at least two (meth)acrylate compounds (C), or at least one (meth) acrylated compound (B) and at least one (meth)acrylate compound (C) are bound by the intermediate of the amine (A2). In general, however, the use of primary amines (A1) comprising at least one primary amino group —$NH_2$ is preferred.

The primary amines (A1) used in the present invention preferably have a weight average molecular weight (MW) of from 31 to 300 Dalton, more preferably from 45 to 250 Dalton. In the present invention, the molecular weight is typically calculated from the chemical formula of the amine (A1).

Suitable amines (A1) respond to formula $R^1$—$NH_2$ (I) wherein $R^1$ represents an alkyl, optionally substituted by hydroxy, alkoxy, tertiary amine and/or aryl.

Amines (A1) may e.g. be selected from one or more of: methylamine, ethylamine, n-propylamine, iso-propylamine, n-butylamine, iso-butylamine, sec-butylamine, tert-butylamine, 3-methylbutylamine, n-hexylamine, n-octylamine, n-dodecylamine, 2-ethylhexylamine, iso-nonylamine, cyclopentylamine, cyclohexylamine, 2-methylcyclohexylamine, benzylamine, 2-(2-amino ethoxy)ethanol, 5-aminopentanol, ethanolamine, 3-amino-1-propanol, iso-propanolamine, 2-amino-2-methyl-1-propanol, 3-(diethylamino)propylamine, N,N-dimethyl aminoneopentylamine, 2-(diethylamino)ethylamine, 1-methyl-4-(diethylamino)butylamine, 2,2-(di-tert-butylamino)ethylamine, 3-(dimethylamino)propylamine, 2-methoxyethylamine, 2-ethoxyethylamine, 3-methoxypropylamine, 1-methoxyisopropylamine, 3-ethoxypropylamine, 3-isopropoxypropylamine, 3-(2-methoxyethoxy)propylamine, 3-(2-ethylhexyloxy)propylamine, furfurylamine, and mixtures thereof.

Preferred are alkylamines (A1) where the alkyl group comprises from 1 to 30 carbon atoms, in particular from 1 to 18 carbon atoms, more in particular from 1 to 14 carbon atoms, optionally substituted by one or more hydroxy groups.

The term "alkyl", as used herein, is defined as including saturated monovalent hydrocarbon radicals having straight, branched or cyclic moieties or combinations thereof.

Especially preferred are n-propylamine, n-butylamine, n-hexylamine, 2-ethylhexylamine, cyclohexylamine, n-octylamine, n-dodecylamine, 2-(2-aminoethoxy)ethanol, 5-aminopentanol, ethanolamine, 3-amino-1-propanol, iso-propanolamine, 2-amino-2-methyl-1-propanol, and mixtures thereof. Particularly preferred are ethanolamine, iso-propanolamine, 2-amino-2-methyl-1-propanol, and mixtures thereof. Most preferred is ethanolamine, especially mono-ethanolamine.

Suitable secondary amines (A2) for use in the present invention respond to formula $R^2HN$—$R^4$—$NHR^3$ (II) wherein $R^2$ and $R^3$ represent, each independently, an alkyl, optionally substituted by hydroxy, alkoxy, tertiary amine and/or aryl, with the proviso that $R^2$ and $R^3$ can be linked in order to form a ring, and $R^4$ is chosen from the group of alkylene and aralkylene chains, containing up to 50 carbon atoms (typically up to 20 carbon atoms) and which may contain from 1 to 20 ether bridges (typically from 1 to 8 ether bridges) and/or from 1 to 3 tertiary amine bridges. The term "alkylene", as used herein is meant to designate bivalent straight, branched or cyclic hydrocarbon radicals. The term "aralkylene", as used herein is meant to designate an alkylene wherein one or more hydrogen groups are replaced by aryl groups.

Preferably, $R^4$ is chosen from the group of bivalent radicals of ethylene, 1,2-propylene, trimethylene, hexamethylene, 2,2-dimethylpropylene, 1-methyltrimethylene, 1,2,3-trimethyltetramethylene, 2-methyl-pentamethylene, 2,2,4-(or 2,4,4-)trimethylhexamethylene, metaxylylene, 3,5,5-trimethylcyclohexyl-1-ene-3-methylene, bis(cyclohexyl-4-ene) methane, bis(4-methylcyclohexyl-3-ene)methane, cyclohexyl-1,3-ene, cyclohexyl-1,4-ene, 1,4-bis(propoxyl-3-ene) butane, N,N-bis(trimethylene)methylamine, 3,6-dioxaoctylene, 3,8-dioxadodecylene, 4,7,10-trioxamidecylene, poly(oxytetramethylene), poly(oxypropylene) with 2 to 15 1,2-propylene oxide units, poly(oxypropylene-co-oxyethylene) with 2 to 15 propylene oxide and 2 to 15 ethylene oxide units, 2,2-dimethylpropylene.

Preferred cyclic secondary amines are diaza-cyclo pentanes, pentenes, hexanes, hexenes, heptanes and heptenes. Especially preferred secondary amines (A2) are 2-methylpiperazine, ditertiobutylethanediamine (also referred to as N,N'-ditertiobutylethanediamine, and mixtures thereof.

By (meth)acrylated diluent (C) is meant to designate in the present invention, a (meth)acrylated compound wherein the urethane(meth)acrylate (B) is soluble or miscible with.

Preferred (meth)acrylated diluents (C) are those which are liquid at room temperature or which present a viscosity of 1 to 2000 mPa·s at 25° C., especially those having a viscosity of 1 to 200 mPa·s. Viscosity measurements in the present invention have been performed according to the method described infra.

Examples of (meth)acrylated diluents (C) that may be used in the present invention are beta-carboxyethyl acrylate, butyl (meth)acrylate, methyl(meth)acrylate, isobutyl (meth)acrylate, 2-ethylhexyl(meth)acrylate, cyclohexyl (meth)acrylate, n-hexyl (meth)acrylate, isobornyl (meth)acrylate, isooctyl (meth)acrylate, n-lauryl (meth)acrylate, octyl/decyl (meth)acrylate, 2-hydroxyethyl(meth)acrylate, phenoxyethyl (meth)acrylate, nonylphenolethoxylate mono(meth)acrylate, 2-(-2-ethoxyethoxy)ethyl(meth)acrylate, 2-butoxyethyl (meth)acrylate, N-vinyl pyrrolidone, 1,6-hexanediol diacrylate (HDDA), pentaerythritoltriacrylate (PETIA), trimethylolpropanetriacrylate (TMPTA), dipropopyleneglycol diacrylate (DPGDA), tripropyleneglycol diacrylate (TPGDA), phenylglycidyletheracrylate, the (meth)acrylic acid ester of tert-decanoic acid glycidyl ester, and possibly the (meth)acrylated ethoxylated and/or propoxylated derivatives thereof (such as (meth)acrylated ethoxylated and/or propoxylated trimethylolpropane, glycerol, neopentylglycol and/or pentaerythritol; ethoxylated and/or propoxylated derivatives of phenoxyethyl(meth)acrylate etc.).

(Meth)acrylated diluents (C) used in the present invention may be selected from one or more mono(meth)acrylates, from one or more di(meth)acrylates and/or from one or more tri(meth)acrylates. They preferably are selected from one or more mono(meth)acrylates and/or from one or more di(meth)acrylates. Preferably these (meth)acrylated diluents do not comprise any beta-hydroxy group.

Particularly preferred are di(meth)acrylates.

Generally (meth)acrylates of polyols, especially diols, are used.

Suited are e.g. 1,6-hexanediol di(meth)acrylate, dipropyleneglycol di(meth)acrylate, tripropyleneglycol di(meth)acrylate, propoxylated glycerine tri(meth)acrylate, and mixtures thereof. Particularly suited are 1,6-hexanediol di(meth)acrylate, dipropopyleneglycol di(meth)acrylate, and mixtures thereof. Acrylates thereof are most preferred.

Urethane(meth)acrylates are well known in the art and commercially available products. By urethane(meth)acrylate (B) is meant to designate in the present invention a compound containing at least one carbamate group corresponding to formula (III) and at least one (meth)acrylate group corresponding to formula (IV) wherein R is an hydrogen atom or a methyl group.

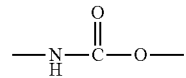

formula (III)

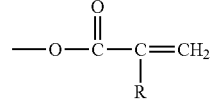

formula (IV)

Preferably the urethane(meth)acrylate (B) used in the present invention is a flexible urethane (meth)acrylate that has an elongation at break of 10 to 500%, more preferably 50 to 300%. The elongation at break is measured by tensile testing of a radiation-cured thin free-film of the urethane (meth)acrylate according to ASTM D 638.

Urethane(meth)acrylates (B) used in the present invention may be aliphatic urethane(meth)acrylates or aromatic urethane(meth)acrylates.

Examples of suitable urethane(meth)acrylates (B) include those commercialized under the names EBECRYL® 204, EBECRYL® 205, EBECRYL® 210, EBECRYL® 230, EBECRYL® 270 etc.

Preferably the urethane(meth)acrylate (B) used in the present invention comprises at least two (meth)acrylate groups and preferably at most six, more preferably at most four (meth)acrylate groups.

Urethane(meth)acrylates (B) as used in the present invention preferably comprise two or three (meth)acrylate groups, more in particular two or three acrylate groups. Particularly suited are urethane di(meth)acrylates, even more preferred are urethane diacrylates.

Urethane(meth)acrylates (B) as used in the present invention typically are obtained by the reaction of:
(a) at least one polyisocyanate,
(b) at least one hydroxy (meth)acrylate, and
(c) optionally, at least one polyol.

The polyols used in the preparation of the urethane(meth)acrylate (B) can be selected from polyester polyols, acrylic polyols, polyether polyols, polyolefin polyols, polycarbonate polyols, and/or mixtures thereof. By polyol is meant herein an alcohol comprising at least two hydroxyl groups and having a weight average molecular weight (Mw) of at least 400 Dalton, as determined by GPC. GPC measurements in the context of the present invention are performed according to the method described infra. Preferred polyols are those having from 2 to 4 hydroxyl groups and a Mw of from 500 to 5000 Dalton. The polyol preferably has a Mw which does not exceed 3000, preferably does not exceed 1000. Particularly preferred are diols such as e.g. polypropyleneglycol.

The polyisocyanates used in the preparation of the urethane(meth)acrylate (B) may be aromatic, cycloaliphatic and/or aliphatic polyisocyanates comprising at least two isocyanate functions and preferably at most six isocyanate functions, more preferably at most 4 isocyanate functions. Preferred are di-isocyanates, such as hexamethylene-diisocyanate (HMDI), isophorone-diisocyanate (IPDI), bis(4-isocyanatocyclohexyl)methane, toluene-diisocyanate (TDI), diphenylmethane-4,4'-diisocyanate or diphenylmethane-2,4'-diisocyanate (MDI), trimethylhexamethylene diisocyanate, tetramethyl-m-xylene diisocyanate; their di-, tri- or oligomers (such as the polymeric diphenylmethane diisocyanate Mondur® MR L or the isomer mixture of diphenylmethane diisocyanate (MDI) containing a high percentage of the 2,4' isomer commercialized under the name Mondur® ML); and/or their adducts with polyols. Optionally, isocyanate functional biurets, allophonates, uretdiones, and isocyanurates of the listed isocyanates may be used. Preferred are isophorone-diisocyanate, bis(4-isocyanatocyclohexyl)methane and toluene-diisocyanate. Most preferred are bis(4-isocyanatocyclohexyl)methane and toluene-diisocyanate.

By a hydroxy(meth)acrylate compound is meant to designate a compound which contains at least one hydroxyl group and at least one (meth)acrylate group. Suitable compounds for use in the present invention are the (meth)acrylic esters of linear or branched polyols in which at least one hydroxy functionality remains free, like hydroxyalkyl(meth)acrylates having 1 to 20 carbon atoms in the alkyl chain. Preferred are monohydroxy alkyl(meth)acrylates comprising from 1 to 20 carbon atoms in the alkyl chain. Examples of suitable compounds include hydroxymethyl (meth)acrylate, hydroxyethyl (meth)acrylate, hydroxypropyl (meth)acrylate, hydroxybutyl (meth)acrylate, glycerol di(meth)acrylate, trimethylolpropane di(meth)acrylate, pentaerythritol tri(meth)acrylate, ditrimethylolpropane tri(meth)acrylate, dipentaerythritol penta (meth)acrylate, caprolactone-hydroxyethyl acrylate adducts and their (poly)ethoxylated and/or (poly)propoxylated equivalents, and mixtures thereof. Acrylates are preferred. Particularly suited are hydroxyethylacrylate and/or hydroxylpropylacrylate.

The mixture used in the present invention for reaction with the amine (A) comprises from 15 to 99% by weight of at least one urethane(meth)acrylate (B) and from 1 to 85% by weight of at least one (meth)acrylated diluent (C). Typically the amount of urethane(meth)acrylate (B) in this mixture is at least 25% by weight, often at least 30% by weight. Typically the amount of (meth)acrylated diluent (C) in this mixture is at most 75% by weight, often at most 70% by weight.

The mixture used in the present invention for reaction with the amine (A) preferably comprises from 30 to 99% by weight of at least one urethane(meth)acrylate (B) and from 1 to 70% by weight of at least one (meth)acrylated diluent (C). The percentages by weight are herein relative to the total weight of the mixture (M) that is used to prepare the amino(meth) acrylates of the invention.

Typically the weight percentages of urethane(meth)acrylates (B) and of (meth)acrylated diluents (C) in the mixture (M) add up to 100%. In the present invention, typically no reagent other than compounds (A), (B) and (C) is used to prepare the amino(meth)acrylates of the invention.

The reaction between (meth)acrylates and amines is known as Michael addition reaction. It takes place by the addition of the amine on a carbon-carbon double bond of the (meth)acrylate. The reaction between the urethane(meth) acrylates and the amine can take place without any catalyst or solvent. The reaction can be carried out at a temperature between –30 to 150° C., the preferred temperature is from 25 to 100° C. Although solvent is not required it may be used to facilitate the heat and mass transfer.

The amino(meth)acrylates according to the present invention are generally obtained from the reaction of an amine (A) with the mixture comprising at least one urethane(meth)acrylate (B) and at least one (meth)acrylated diluent (C) in an amount of amine such that the equivalent ratio of amino groups —N—H from the amine (A) to (meth)acrylic double bounds provided by the urethane(meth)acrylate (B) and the (meth)acrylated diluent (C) is from 0.01 to 0.9. Hence, in case that a primary amine (A1) is used, the number of —N—H groups is calculated as being twice the number of —NH$_2$ groups provided by the primary amine. Preferably the amount of amine (A) is such that the equivalent ratio of amino groups —N—H of (A) to (meth)acrylic double bonds provided by (B) and (C) is at least 0.05, more preferably at least 0.1. The equivalent ratio does preferably not exceed 0.8, more preferably it does not exceed 0.7. It can be beneficial that the equivalent ratio does not exceed 0.5, more preferably does not exceed 0.3.

Without wishing to be bound to any mechanism, it is believed that the use of amines (A1) and (A2) in the stoichiometry ranges according to the present invention allows obtaining amino(meth)acrylates that are chain extended at such an extent that they are characterized by an optimum balance between an acceptable viscosity and a good abrasion resistance.

The present invention also relates to a method for the preparation of amino(meth)acrylates such as herein described wherein at least one amine (A) is reacted with a mixture comprising from 15 to 99% by weight of at least one urethane (meth)acrylate (B) as specified above and from 1 to 85% by weight of at least one (meth)acrylated diluent (C). Typically the amount of urethane(meth)acrylate (B) in this mixture is at least 25% by weight, often at least 30% by weight. Typically the amount of (meth)acrylated diluent (C) in this mixture is at most 75% by weight, often at most 70% by weight.

Preferably the mixture used in the preparation of amino (meth)acrylates according to the invention comprises from 30 to 99% by weight of at least one urethane(meth)acrylate (B) and from 1 to 70% by weight of at least one (meth)acrylated diluent (C). The percentages by weight are herein relative to the total weight of the mixture (M) used to prepare the amino (meth)acrylates of the invention.

Typically the sum of the weight percentages of urethane (meth)acrylates (B) and of (meth)acrylated diluents (C) in the mixture adds up to 100%. In the present invention, typically no reagents other than compounds (A), (B) and (C) are used to prepare the amino(meth)acrylates of the invention.

Generally a mixture of different amino(meth)acrylates, optionally in the presence of residual (unreacted) (meth)acrylated compounds (B) and/or (C) are obtained.

The completion of the reaction can be followed for example by measuring the amount of free amine—see e.g. the method given infra. At the completion of the reaction, the amino(meth)acrylate can be recovered as residue product; however, in some instances recovery by conventional distillation and fractionation procedures is possible. Preferably the residue of free amine is eliminated from the amino(meth) acrylate at levels below 1000 ppm, more preferably at levels below 500 ppm, most preferably at levels below 400 ppm. Elimination of the free amine can be done by any method suitable therefore, such as stripping, for example with air or nitrogen under reduced pressure. Although it is possible to separate the unreacted (meth)acrylated compounds (B) and/ or (C) from the amino(meth)acrylate, generally the (meth) acrylated compounds (B) and/or (C) are not separated from the amino(meth)acrylate before further use in radiation curable compositions.

To prevent premature (meth)acrylate polymerization various inhibitors or stabilizers may also be added during or after the reaction. Typical inhibitors such aromatic or aliphatic phosphites can be used.

The amino(meth)acrylates of the present invention preferably have a viscosity of 100 to 50000 mPa·s at 25° C. Preferably the viscosity is at most 20000 mPa·s at 25° C. Preferably the viscosity is at least 2000 mPa·s at 25° C.

The amino(meth)acrylates of the present invention preferably have a nitrogen content of at least 0.1%, more preferably of at least 1.0%, by weight. The nitrogen content does preferably not exceed 5.0% by weight, more preferably not 3.5%. Values given here are theoretical values that are calculated starting from the amine and the amount in which it is used to prepare amino(meth)acrylates of the invention. The present invention also relates to the use of such amino(meth)acrylates, especially in the radiation curable compositions such as described here below.

The amino(meth)acrylates according to the present invention have been found to be very effective in UV/EB curing and can be used alone or along with other (meth)acrylated compounds. The amino(meth)acrylates are readily cured by ultraviolet light radiation or electron beam radiation.

The amino(meth)acrylates according to the invention present a good reactivity under exposure to radiation.

The amino(meth)acrylates according to the invention permit to obtain coatings with a good abrasion and scratch resistance, advantageously in combination with a good reactivity. Reactivity during exposure to radiation (in casu UV light: 2 medium pressure mercury H bulbs, 120 w/cm) obtained with a coating composition according to the invention typically lies between 20 and 45 m/min, more in particular between 25 and 35 m/min, i.e. the typical speed of state of the art production lines.

The amino(meth)acrylates according to the invention even permit to obtain coatings with an increased abrasion resistance. Other characteristics like chemical and thermal resistance, adhesion and hardness, flexibility etc advantageously were not negatively impacted by an increase in abrasion resistance.

The amino(meth)acrylates according to the invention advantageously permit to obtain coatings that are characterized by an optimum balance between an acceptable viscosity and a good abrasion resistance.

Yellowing tendency of the amino(meth)acrylates according to the invention, under forced conditions (UV-Vitalux 300 W lamp, 72 hours), was found to be similar to slightly better compared to the same resins made without amination.

The amino(meth)acrylates according to the invention are especially useful for the preparation of wood coatings, in particular for the preparation of sealer compositions for wood floors, more in particular parquet and laminate floors. Intercoat adhesion proved excellent when using a radiation curable composition according to the invention. The amino (meth)acrylates of the invention are also suited for use on other types of floorings such as resilient floorings.

The amino(meth)acrylates according to the present invention can be used in radiation curable compositions comprising usual ingredients as sole radiation curable compound or along with other radiation curable, especially (meth)acrylated compounds.

The present invention relates to a radiation curable composition comprising at least one amino(meth)acrylate according to the invention.

The invention in particular relates to a radiation curable composition containing at least 5% by weight of at least one amino(meth)acrylate according to the invention. Preferably the composition comprises at least 10% by weight of said amino(meth)acrylate. The amount of amino(meth)acrylate usually does not exceed 99% by weight. Weight percentages are herein relative to the total weight of the radiation curable composition.

The radiation curable composition according to the invention may contain besides the amino(meth)acrylate(s), at least one radiation curable polymer precursor other than the amino (meth)acrylate(s) as described herein. The term polymer precursor is used to designate a monomer or oligomer or mixtures thereof which have suitable polymerisable functionality, preferably comprising at the chains ends or laterally along the chain, one or more (meth)acrylate or vinyl groups. This radiation curable polymer precursor is generally a monomer or an oligomer comprising one or more (meth) acrylate or vinyl groups. Preferably this radiation curable polymer precursor is a (meth)acrylated oligomer and/or a (meth)acrylated monomer.

The radiation curable composition according to the invention may for instance further comprise at least one (meth) acrylated diluent (D), which may be same or may be different from the (meth)acrylated diluent (C) as described above. By (meth)acrylated diluent (D) is meant to designate in the present invention, a (meth)acrylated compound wherein the amino(meth)acrylate of the present invention is soluble or miscible with. This (meth)acrylated diluent (D) is typically a low molecular weight reactive diluent. These low molecular weight reactive diluents typically have a weight average molecular weight of at most 1000 Dalton. In the present invention, the molecular weight of such diluents is typically calculated from the chemical formula of the diluent.

Examples of such low molecular weight (meth)acrylated diluents (D) include (meth)acrylic acid, beta-carboxyethyl acrylate, butyl(meth)acrylate, methyl(meth)acrylate, iso-butyl (meth)acrylate, 2-ethylhexyl(meth)acrylate, cyclohexyl (meth)acrylate, n-hexyl (meth)acrylate, iso-bornyl (meth) acrylate, iso-octyl (meth)acrylate, n-lauryl (meth)acrylate, octyl/decyl (meth)acrylate, 2-hydroxyethyl(meth)acrylate, phenoxyethyl(meth)acrylate, nonylphenolethoxylate mono (meth)acrylate, 2-(-2-ethoxyethoxy)ethyl(meth)acrylate, 2-butoxyethyl (meth)acrylate, the (meth)acrylic acid ester of tert-decanoic acid glycidyl ester, N-vinyl pyrrolidone, 1,6-hexanedioldiacrylate (HDDA), pentaerythritoltriacrylate (PETIA), trimethylolpropanetriacrylate (TMPTA), phenylglycidyletheracrylate, dipropyleneglycoldiacrylate (DPGDA), tripropyleneglycoldiacrylate (TPGDA), and the (meth)acrylated ethoxylated and/or propoxylated derivatives thereof (such as (meth)acrylated ethoxylated and/or propoxylated trimethylolpropane, glycerol, neopentylglycol and/or pentaerythritol; ethoxylated and/or propoxylated derivatives of phenoxyethyl(meth)acrylate etc.).

(Meth)acrylated diluents (D), if used in the present invention, preferably are selected from one or more mono(meth) acrylates and/or from one or more di(meth)acrylates. Preferably these (meth)acrylated diluents do not comprise any beta-hydroxy group.

In an embodiment according to the invention, the optional (meth)acrylated diluent (D) is selected from one or more mono(meth)acrylates and, optionally, from one or more di(meth)acrylates. Examples of suitable and preferred di(meth)acrylates are given above. Preferably the amount of mono(meth)acrylated diluents (D), on the total weight of mono(meth)acrylated and di(meth)acrylated diluents (D), is at least 20% by weight, more preferably at least 35% by weight, even more preferably at least 50% by weight, most preferably at least 80% by weight.

In a particular embodiment according to the invention, the optional (meth)acrylated diluent (D) is selected from one or more mono(meth)acrylates.

Examples of suitable mono(meth)acrylates (D) for use in the present invention include octyl/decyl (meth)acrylate, phenoxyethyl(meth)acrylate, nonylphenolethoxylate mono (meth)acrylate, 2-(-2-ethoxyethoxy)ethyl(meth)acrylate, the (meth)acrylic acid ester of tert-decanoic acid glycidyl ester, ethoxylated and/or propoxylated derivatives of phenoxyethyl (meth)acrylate, and mixtures of any of these. Preferred are those that do not comprise any beta-hydroxy group.

Particularly preferred are the ethoxylated and/or propoxylated derivatives of phenoxyethyl(meth)acrylate, more in particular the ethoxylated derivatives of phenoxyethyl(meth) acrylate. Most preferred is the ethoxylated phenoxyethyl monoacrylate (EPEA).

Preferred (meth)acrylated diluents (D) for use in the present invention are those which are liquid at room temperature or which present a viscosity of 1 to 2000 mPa·s at 25° C., especially those having a viscosity of 1 to 200 mPa·s.

When used, the quantity of (meth)acrylated diluents (D) in the radiation curable composition according to the invention is generally at least 2% by weight, preferably at least 5% by weight, more preferably at least 10% by weight. The quantity of (meth)acrylated diluents (D) does usually not exceed 40% by weight, preferably it does not exceed 15% by weight. Weight percentages are herein relative to the total weight of the radiation curable composition.

In yet another embodiment of the invention, the radiation curable composition according to the invention does not comprise any (meth)acrylated diluent (D).

Alternatively, or in addition to the above optional (meth) acrylated diluents (D), the radiation curable composition of the invention may also comprise one or more oligomers. Preferred oligomers include (meth)acrylated acrylic oligomers, aromatic acid (meth)acrylates, (meth)acrylated polybutadienes, (meth)acrylated polyesters, urethane (meth)acrylates, epoxy (meth)acrylates and hyperbranched (meth) acrylates such as hyperbranched polyester polyol (meth) acrylates.

Preferred oligomers are those having a weight average molecular weight of at least 1000 and not more than 6000 Dalton, as determined by GPC—see infra for the method used.

When used, the quantity of oligomer in the radiation curable composition according to the invention is generally at least 5% by weight, preferably at least 10% by weight. The quantity of oligomer does usually not exceed 50% by weight, preferably it does not exceed 40% by weight. Weight percentages are herein relative to the total weight of the radiation curable composition.

The radiation curable compositions used in the present invention generally comprise at least one photoinitiator, that is a compound that can generate radicals by absorption of light, typically UV light. Generally, the amount of photoinitiator in the composition is comprised between 0 and 15% by weight, preferably between 0.01 and 8% by weight. Weight percentages are herein relative to the total weight of the radiation curable composition.

Alternatively, the radiation curable composition without photoinitiator can be cured, generally by electron beam.

The radiation curable composition can also contain additives commonly used in the art, such as substrate wetting agents, anti-foam agents, dispersing agents, flow modification agents, slip agents, plasticizing diluents, fire retardant agents, UV-protection agents, adhesion promoters, antioxidants, reinforcing agents and stabilizers. The total amount of commonly used additives usually does not exceed 10% by weight. Preferably, the composition comprises from 0.01 to 5% by weight of commonly used additives as described here above. Weight percentages are herein relative to the total weight of the radiation curable composition.

Where needed, the radiation curable composition can also contain one or more pigment or colorant. The colorants and pigments usable in the compositions of the invention can be any pigment or colorant known in the art. A list of suitable pigments can be found in the Color Index. More particularly, those pigments may be cited such as Process Yellow 13 (Diarylide Yellow—Irgalite BAW of Ciba, Permanent GR of Clariant), Process Magenta Pigment 57 (Bona Calcium—Ilobona 4BY of Sun, Irgalite SMA of Ciba), Process Blue 15.3 (Copper Phthalocyanine—Irgalite GLO of Ciba, Hostaperm Blue B2G of Clariant), Process Black 7 (Oxidised Carbon Black—Special Black 250; Special Black 350 of Degussa), etc. The colorants and/or pigments are preferably used at 0-50% by weight of the total weight of the radiation curable composition, more preferably at 0-40% by weight.

The radiation curable composition may also comprise from 0 to 20% by weight of fillers or non reactive diluents or solvents. From 0 to 20% by weight of inert resins may also be used in the radiation curable composition. Inert resins are resins that do not take part in the radiation or EB induced polymerization reaction. Examples of such inert resins typically include hydrocarbons (such as styrene based hydrocarbon resins), acrylics (such as acrylic (co)polymers), (poly) urethane resins, polyethylenevinylacetate resins, polyvinylchloride resins, chlorinated polyolefin resins and/or ketone resins.

The radiation curable compositions can be produced by mixing the selected components thereof by conventional known methods. The blend can be heated, if desired, to facilitate mixing.

The radiation curable compositions of the present invention can be used for the making of coatings, in particular industrial coatings, adhesives, inks and varnishes. By inks is meant to understand liquid inks as well as paste inks.

The present invention therefore relates to the use of an amino(meth)acrylate, or of a radiation curable composition according to the invention in a radiation curable composition suitable for the preparation of a coating, adhesive, ink or varnish.

An aspect of the invention concerns a coating, adhesive, ink or varnish prepared from an amino(meth)acrylate, or from a radiation curable composition according to the invention.

The present invention also relates to the use of an amino (meth)acrylate, or of a radiation curable composition according to the invention in a radiation curable composition suitable for use on wood (plain or veneer).

The present invention also relates to the use of an amino (meth)acrylate, or of a radiation curable composition according to the invention in a radiation curable composition suitable for use on floorings and more particular on wood floorings (plain or veneer).

The radiation curable compositions of the present invention are particularly suited for use in flooring applications. Floorings that may e.g. be coated with a radiation curable composition of the present invention include wood floorings (such as parquet floors and laminate floors) and resilient floorings. Resilient floorings may be made from vinyl, polyolefin, linoleum, rubber or cork.

The radiation curable composition of the present invention is particularly suited for the making of sealer compositions to be used on such floorings, in particular wood floorings and more in particular parquet and laminate floors.

The present invention also relates to process for coating a flooring, more in particular a wood flooring (such as parquet floors and laminate floors), which process comprises applying to a floor substrate one or more layers of a radiation curable composition according to the invention, and curing the applied composition by exposure to radiation (such as actinic radiation, UV light, ionizing radiation and/or electron beam).

When used as a sealer composition for wood (such as a wood floor), the coating composition of the invention preferably is a clear coat comprising no pigments and/or colorants. The coating composition of the present invention protects the natural wood (plain or veneer) from staining and wear. A clear coating will enhance the wood colour and structure.

Wood coatings typically consist of different layers, each with special characteristics. A typical system comprises (or consists of) a primer, one or more layers (preferably three) of a sealer and then a top coat. For an optimum performance of the total coating systems, an excellent intercoat adhesion is highly desirable.

Accordingly, in the process according to the invention the step of applying one or more layers of a radiation curable composition according to the invention is preferably preceded by a step of applying a primer coat and is preferably followed by a step of applying a top coat. Typically the process according to the invention also comprises one or more sanding steps to improve performances such as adherence. Sanding and/or undercuring were found to improve intercoat adhesion.

The primer coat that may be applied typically has a coat weight of about 5-10 g/m$^2$. The substrate is preferably slightly sanded before application of the primer coat.

The sealer coat typically is a heavy coat, with a typical weight of at least 10 g/m$^2$. For parquet coatings it may be desirable to have a total sealer coating weight of 60-75 g/m$^2$.

Such heavy coat is difficult to be applied in one step. Moreover, mechanical properties will be better if several coats are applied. Typically three to four different sealer layers of each about 25-10 g/m$^2$ are applied. Usually only the first and the last sealer coat layer is fully cured in order to improve the sandability (e.g. using 2 medium pressure mercury lamp H-bulb 120 w/cm 18 m/min). Other sealer coat layers are typically under-cured or gelled, by exposure to e.g. low UV power (e.g. using medium pressure mercury lamp H bulb 120 W/cm$^{-18}$ m/min).

In order to get a nice appearance, gloss and stain resistance, a top coat layer is usually applied after application and curing of the one or more sealer coat layers. Preferably the substrate is sanded (e.g. mechanically) before applying the top coat layer on the coated substrate. Typically the topcoat has a weight of 8-20 g/m$^2$. The topcoat may be applied as a single layer with a weight of 8-10 g/m$^2$. Alternatively, the top coat may consist of 2 different layers, the first typically having a weight of 10 g/m$^2$, said first layer being gelled or under-cured before application of a second layer with a weight of 5 g/m$^2$, followed by full curing.

The different coatings and coating layers can be applied via standard roller coating.

The present invention also relates to a process for preparing a coated article comprising a step wherein the article is coated with a radiation curable composition of the present invention. A further aspect of the invention relates to an article coated, partially or entirely, with a radiation curable composition of the present invention.

The present invention is illustrated by the following, non-limiting examples.

EXAMPLE 1

60 kg of an aromatic urethane triacrylate (oligomer 1) obtained by the reaction of hydroxyethylacrylate, toluene diisocyanate and triol initiated polypropyleneglycol (30000 mPa·s @ 25°, MW=2000 g/mol) were mixed with 20 kg dipropyleneglycol diacrylate, 20 kg tripropyleneglycol diacrylate and 1 kg monoethanolamine. The reaction was performed at a temperature not exceeding 90° C. until a residual amine content below 500 ppm is reached. The characteristics of the obtained resin are presented in table 1.

EXAMPLE 2

Resins of example 2 are obtained according to the same method as described in example 1. The composition and amounts are adapted as presented in table 1. The characteristics of the obtained resins are presented in table 1, as well.

EXAMPLE 3

Resins of example 3 are obtained according to the same method as described in example 1, though using an aromatic urethane diacrylate (oligomer 2) obtained by the reaction of hydroxyethylacrylate, toluene diisocyanate and diol initiated polypropyleneglycol (3900 mPa·s @60°, MW=1500 g/mol). The composition and amounts are adapted as presented in table 1. The characteristics of the obtained resins are presented in table 1, as well

EXAMPLE 4

Resins of example 4 are obtained according to the same method as described in example 3. However, when a residual amine content below 1000 ppm is reached, a defined amount of a second diluting monomer is added and the whole is mixed until a homogeneous medium is obtained. The composition and amounts are adapted as presented in table 1. The characteristics of the obtained resins are presented in table 1.

EXAMPLE 5

234.5 kg of an aromatic urethane diacrylate obtained by the reaction of hydroxyethylacrylate, toluene diisocyanate and diol initiated polypropyleneglycol (oligomer 2) were mixed with 40 kg dipropyleneglycol diacrylate before the addition of the amine. When a residual amine content below 500 ppm is reached, 15 kg of dipropyleneglycol diacrylate together with a defined amount of a second diluting monomers is added and the whole is mixed until a homogeneous medium is obtained. The composition and amounts are adapted as presented in table 1. The characteristics of the obtained resins are presented in table 1.

EXAMPLE 6

Resins of example 6 are obtained according to the same method as described in example 4, though using an aliphatic urethane diacrylate (oligomer 3) obtained by the reaction of hydroxyethylacrylate, isophorone diisocyanate and diol initiated polypropyleneglycol (3080 mPa·s @60°, MW=1200 g/mol) and using propoxylated glycerine triacrylate. The composition and amounts are adapted as presented in table 1. The characteristics of the obtained resins are presented in table 1, as well.

EXAMPLE 7

Resins of example 7 are obtained according to the same method as described in example 4, though using an aliphatic diamine N,N'-ditertiobutylethanediamine (DTBEDA) instead of the monoethanol amine. The composition and amounts are adapted as presented in table 1. The characteristics of the obtained resins are presented in table 1, as well.

EXAMPLES 8 TO 14 AND 15R

UV curable sealer formulations are prepared by mixing at 25° C. the ingredients as described in table 2. The formulations are then evaluated in terms of reactivity and the results are presented in table 2. Parts are parts by weight.

EXAMPLES 16 TO 22 AND 23R

Sealers are prepared according to the following protocol.

15 g/m² wet of the UV curable primer formulation of example 24 are applied on slightly sanded (150/180 aluminium oxide sanding paper) beech wood. The primer is cured with a mercury UV lamp of 120 W/cm at 18 m/min.

Then, 3 layers of the UV curable sealer formulations of table 2 are step by step applied by roller coater in 20-22 μm thickness, according to table 3. First and third layers are cured with two mercury UV lamps of 120 W/cm at 18 m/min, and slightly sanded by hand. The second layer is cured with one mercury UV lamp of 120 W/cm at 18 m/min and is not sanded.

Finally, the UV curable topcoat formulation of example 25 is applied in 8 μm thickness and fully cured with 2 lamps 80 W/cm at 5 m/min.

The coated beech wood samples are evaluated for adhesion, Hamberger Höbel, grit feeder, cold-check and yellowing. The results obtained are presented in Table 3.

EXAMPLE 24

A UV curable primer formulation is prepared by mixing at 25° C. the following ingredients. Parts are parts by weight:
100 parts UCECOAT® 6558
10 parts EBECRYL® 12
1.5 parts ADDITOL® BCPK (photoinitiator commercialized by Cytec)

EXAMPLE 25

A UV curable topcoat formulation is prepared by mixing at 25° C. the following ingredients. Parts are parts by weight:
30 parts EBECRYL® 265
10 parts EBECRYL® 810
42 parts DPGDA
3 parts ADDITOL® BP (photoinitiator commercialized by Cytec)
2 parts ADDITOL® HDMAP (photoinitiator commercialized by Cytec)
8 parts SYLOID® 162C (matting agent from Grace)
2 parts Lancowax PP 1362 (polypropylene wax from Langer & Co)
1 part DOW CORNING PA-11 (flow additive from Dow Corning)
2 parts ACEMATT® TS100 (matting agent from Evonik)
HDMAP=2-Hydroxy-2-methyl-1-phenyl propanone In the evaluation of properties of the amino(meth)acrylates and radiation curable compositions according to the invention the following test methods were used, throughout the invention and in the examples:

Amine contents: amine content is determined by reacting quantatively the primary and secondary amines with CS2. The resulting thiocarbamic acid is potentiometrically titrated with NaOH. The amine content value is expressed in ppm.

Cone & plate viscosity: viscosity is measured with a rotational viscometer at 25° C. with defined shear rate of 20 s-1, according to DIN EN ISO 3219. The viscosity value is expressed in mPa·s.

Reactivity: a film of 25 μm is applied on white non absorbing paper and exposed to UV radiations from a 80 W/cm non focalized medium pressure mercury lamp at a defined conveyer speed. The conveyer speed is varied in order to determine the maximum conveyer speed to be used to obtain a fully cured film. The fully cured character of the film is assessed by putting some talc on the surface and rubbing with a finger and then with a cotton. As long as a mat aspect is observed, the film is not fully cured and the conveyer speed must be lowered. The coating is also submitted to 50 double rubs with a wad of cotton drenched in acetone. A fully cured film is not visually affected by this test. The UV-dose (expressed in conveyer speed (m/min) with determined lamp power (W/m)) necessary to pass the two tests is referred to as the reactivity of the coating.

Adhesion: a film of 20-22 μm is applied on the primer and fully cured as described in the reactivity method. A square pattern is engraved in the coating with a cutter. A string of adhesive tape (Tesa 4104) is pressed on the surface and the interlayer is degassed. The tape is then snatched off. Based on the number of squares removed by the tape, a value of adhesion is given: 0B (100% of the squares removed), 1B (65-35% of the squares removed), 2B (35-15% of the squares removed), 3B (15-5% of the square removed), 4B (less than 5% of the squares removed, 5B (0%).

Hamberger-Höbel (coin test): a full coating system is applied on sanded beech, cured and placed on the Hamberger Höbel tester. The apparatus is equipped with a screw that can be turned in such a way that the pressure of a coin on the coating can be varied. The pressure is increased step by step until a scratch of a few centimeters is made on the coated surface. The higher the applied pressure, the better the scratch resistance. The scratch resistance is expressed in Newton.

Grit feeder: This method is based on the standard test method ASTM F510-93 and uses a Taber abrader 5150 with leather-covered wheels (S-39); sand used in the test is of the type Alodur ESK 240 EN 14354 from Treibacher. A full coating system is applied on sanded beech and cured. All equipment and substrates are conditioned at least 24 hours in the conditioned room (21±1° C., 50±5% relative humidity) before testing. The coated substrates are abraded in steps of 500 cycles until spots appear where the coating is completely removed (initial point). The initial point is reached when blues spots are formed on the test specimen after application of a methylene blue solution. After determination of the initial point, abrasion is carried out for another 500 cycles. Again, a methyleneblue solution is applied for visual comparison. Abrasion is measured by weight loss (in mg, accuracy of ±0.1 mg) after each 500 cycles step.

Cold-check: a full coating system is applied on sanded beech and cured. The coated substrate is submitted to 2×25 cycles of 1 hour at −20° C. and 1 hour at +70° C. The coating passes the test when remaining free of cracks.

Yellowing: a film of 25 μm is applied on white non absorbing paper, cured and exposed to the UV light of an Ultra-Vialux 300 W lamp in a completely closed drum. The distance between the lamp and the samples is 50 cm. Yellowing (delta b) is measured with an apparatus type Supercolor after 96 hours of exposition and compared with the initial yellowing (before exposure).

Weight average molecular weight and number average molecular weight determination by GPC: The number-average molecular weight (Mn), the weight-average molecular weight (Mw) and polydispersity are typically determined by conventional gel permeation chromatography (GPC) with polystyrene standards EasyCal from Polymer Laboratories (Molecular Weight range: 200-400.000 g/mol). A small portion of sample is dissolved in tetrahydrofuran (THF) and injected into a liquid chromatograph (Merck-Hitachi L7100) equipped with 3 PLGel Mixed-D LS polystyrene divinylbenzene GPC columns (300 mm×7.5 mm×5 μm). The components of the sample are separated by the GPC columns based on their molecular size in solution and detected by a Refractive Index detector. Data were gathered and processed by Polymer Laboratories Cirrus GPC software.

TABLE 1

Composition and characteristics of the resins

|  | Ex. 1 | Ex. 2 | Ex. 3 | Ex. 4 | Ex. 5 | Ex. 6 | Ex. 7 |
|---|---|---|---|---|---|---|---|
| Oligomer (B) | | | | | | | |
| Oligomer 1 | 60 kg | 56.2 kg | | | | | |
| Oligomer 2 | | | 65 kg | 376.2 kg | 234.5 kg | | 61.3 kg |
| Oligomer 3 | | | | | | 63.8 kg | |
| (meth)acrylated diluent (C) | | | | | | | |
| DPGDA | 20 kg | 25 kg | 35 kg | 174 kg | 55 kg | | 28.8 kg |
| TPGDA | 20 kg | 18.8 kg | | | | | |
| OTA 480 | | | | | | 29.5 kg | |
| Amine (A) | | | | | | | |
| MEA | 1 kg | 2 kg | 2 kg | 11.3 kg | 7 kg | 1.9 kg | |
| DTBEDA | | | | | | | 5.3 kg |
| (meth)acrylated diluent (D) | | | | | | | |
| DPGDA | | | | | 107 kg | | |
| EPEA | | | | 27.9 kg | 17.5 kg | 4.7 kg | 4.6 kg |
| Viscosity (mPa · s) | 6060 | 6620 | 6630 | 6150 | 7797 | 23263 | |
| Free amine content of final product (ppm) | <500 | <500 | <500 | <500 | <500 | <500 | |

Oligomer 1: aromatic urethane triacrylate obtained by the reaction of hydroxyethylacrylate, toluene diisocyanate and triol initiated polypropyleneglycol.
Oligomer 2: aromatic urethane diacrylate obtained by the reaction of hydroxyethylacrylate, toluene diisocyanate and diol initiated polypropyleneglycol
Oligomer 3: aliphatic urethane diacrylate obtained by the reaction of hydroxyethylacrylate, isophorone diisocyanate and diol initiated polypropyleneglycol
DPGDA: dipropyleneglycol diacrylate
TPGDA: tripropyleneglycol diacrylate
OTA480: propoxylated glycerine triacrylate
EPEA: ethoxylated phenoxyethylacrylate;
MEA: monoethanolamine
DTBEDA: N,N'-ditertiobutylethanediamine

TABLE 2 sealer formulations

|  | Ex. 8 | Ex. 9 | Ex. 10 | Ex. 11 | Ex. 12 | Ex. 13 | Ex. 14 | Ex. 15R |
|---|---|---|---|---|---|---|---|---|
| Resin | Ex. 1 | Ex. 2 | Ex. 3 | Ex. 4 | Ex. 5 | Ex. 6 | Ex. 7 | Oligomer 2 |
| (parts) | (100) | (100) | (100) | (100) | (100) | (100) | (100) | (75) |
| DPGDA (parts) | | | | | | | | 25 |
| ADDITOL ® BCPK (parts) | 4 | 4 | 4 | 4 | 4 | 4 | 4 | 4 |
| Reactivity (m/min) | 30 | 40 | 35 | 30 | 30 | 25 | 10 | 15 |

TABLE 3

Sample evaluation

|  | Ex. 16 | Ex. 17 | Ex. 18 | Ex. 19 | Ex. 20 | Ex. 21 | Ex. 22 | Ex. 23R |
|---|---|---|---|---|---|---|---|---|
| Based on sealer of | Ex. 8 | Ex. 9 | Ex. 10 | Ex. 11 | Ex. 12 | Ex. 13 | Ex. 14 | Ex. 15R |
| Adhesion (0B-5B) | 5B | 5B | 5B | 5B | 5B | 5B | 5B | 5B |
| Hamberger Hobel (N) | 30 | 30 | 30 | 31 | 33 | 29 | >30 | 23-30 |
| Grit feeder (mg) | 151 | 158 | 103 | 95 | 108 | 99 | 108 | 118 |
| Cold-check (pass or fail) | — | — | Pass | Pass | Pass | Pass | Pass | Pass |
| Yellowing (delta b) | 8.4 | 7.8 | 8.0 | 7.0 | 8.1 | — | — | 8.9 |

The results in Tables 2 and 3 show that the amino(meth)acrylates according to the invention combine an improved reactivity with an excellent adhesion, scratch and abrasion resistance. The amino(meth)acrylates of the invention further permit to obtain coatings with an improved abrasion resistance. The amino(meth)acrylates of the invention were found to have a yellowing slightly better compared to a coating based on a non aminated resin like Comparative example 23R.

The invention claimed is:

1. A radiation curable coating composition comprising from 5% to 99% by weight of at least one amino(meth)acrylate obtained from the reaction of at least one amine (A) with a mixture comprising from 15 to 99% by weight of at least one urethane(meth)acrylate (B) and from 1 to 85% by weight of at least one (meth)acrylated diluent (C), wherein the amine (A) is selected from primary amines (A1) comprising at least one primary amino group —$NH_2$ and/or from secondary amines (A2) comprising at least two secondary amino groups —NH, and further comprising at least one (meth)acrylated diluent (D).

2. The composition according to claim 1 wherein the (meth)acrylated diluent (D) is selected from di(meth)acrylates and/or from mono(meth)acrylates.

3. The composition according to claim 1 wherein the (meth)acrylated diluent (D) is a mono(meth)acrylate.

4. A process for coating a floor which process comprises applying to a floor substrate one or more layers of a radiation curable composition according to claim 1, and curing the applied composition by exposure to radiation.

5. The process according to claim 4 wherein the step of applying one or more layers of the composition is preceded by a step of applying a primer coat and is followed by a step of applying a top coat.

6. The process according to claim 4 wherein the floor is a wood floor.

7. The radiation curable coating composition according to claim 1 wherein the amine (A1) responds to formula $R^1$—$NH_2$ wherein $R^1$ is an alkyl, optionally substituted by hydroxyl, alkoxy, tertiary amine and/or aryl.

8. The radiation curable coating composition according to claim 1 wherein the urethane(meth)acrylate (B) comprises from 2 to 4 (meth)acrylate functions.

9. The radiation curable coating composition according to claim 1 wherein the urethane(meth)acrylate (B) is a urethane di(meth)acrylate.

10. The radiation curable coating composition according to claim 1 wherein the (meth)acrylated diluent (C) is selected from tri(meth)acrylates, from di(meth)acrylates and/or from mono(meth)acrylates.

11. The radiation curable coating composition according to claim 1 wherein the (meth)acrylated diluent (C) is a di(meth)acrylate.

12. The radiation curable coating composition according to claim 1 wherein the amount of amine (A) is such that the equivalent ratio of amino groups —N—H provided by the amine (A) to the (meth)acrylic double bounds provided by the urethane(meth)acrylate (B) and (meth)acrylated diluent (C) is from 0.1 to 0.9.

13. A coating, adhesive, ink or varnish prepared from the radiation curable coating composition according to claim 1.

* * * * *